US00PP33989P2

(12) United States Plant Patent
Losert

(10) Patent No.: US PP33,989 P2
(45) Date of Patent: Mar. 1, 2022

(54) ***CALIBRACHOA* PLANT NAMED 'KLECA20810'**

(50) Latin Name: ***Calibrachoa* sp.**
Varietal Denomination: KLECA20810

(71) Applicant: Klemm+Sohn GmbH & Co. KG, Stuttgart (DE)

(72) Inventor: Dominik Losert, Aspach (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/386,172

(22) Filed: Jul. 27, 2021

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC ... A01H 5/02; A01H 5/00; A01H 5/12; A01H 6/82; A01H 6/821
See application file for complete search history.

*Primary Examiner* — June Hwu
(74) *Attorney, Agent, or Firm* — Weatherly IP Solutions, LLC; Barbara Campbell

(57) ABSTRACT

A new *Calibrachoa* plant designated 'KLECA20810' particularly distinguished by a semi-trailing plant habit, and pink flowers with purple centers and yellow stripes, is disclosed.

1 Drawing Sheet

Genus and species: *Calibrachoa* sp.
Variety denomination: 'KLECA20810'.

BACKGROUND OF THE NEW PLANT

The present invention comprises a new and distinct variety of *Calibrachoa*, botanically known as *Calibrachoa* sp., and hereinafter referred to by the variety name 'KLECA20810'. 'KLECA20810' originated from a controlled cross in August 2017 in Stuttgart, Germany between the female *Calibrachoa* parent 'KLECA17029' (U.S. Plant Pat. No. 30,836) and the proprietary male *Calibrachoa* 'CA-2016-8001' (unpatented). Progeny from the cross were planted and a single plant was selected in May 2018 in Stuttgart, Germany.

'KLECA20810' has been found to reproduce true to type in successive generations of asexual propagation in Stuttgart, Germany via vegetative tip cuttings.

SUMMARY

The following are the most outstanding and distinguishing characteristics of 'KLECA20810' when grown under normal horticultural practices in Stuttgart, Germany and Latina, Italy.

1. A semi-trailing plant habit; and
2. Pink flowers with purple centers and yellow stripes.

DESCRIPTION OF THE PHOTOGRAPH

This new *Calibrachoa* plant is illustrated by the accompanying photograph of a plant grown outdoors in Stuttgart, Germany. The photograph shows the whole plant, including the flowers and foliage and buds. The colors shown are as true as can be reasonably obtained by conventional photographic procedures. The photograph is of a plant that is 12-weeks-old, taken indoors in May 2019 in Stuttgart, Germany.

DESCRIPTION OF THE NEW VARIETY

The following detailed descriptions set forth the distinctive characteristics of 'KLECA20810'. The data which define these characteristics were collected from asexual reproductions carried out in Latina, Italy. Data was collected on plants grown 14-weeks since potting in a greenhouse with no pinching and using BONZI. Color references are to The R.H.S. Colour Chart of The Royal Horticultural Society of London (R.H.S.), 5$^{th}$ edition (2007).

Classification:
- *Family*.—Solanaceae.
- *Botanical*.—*Calibrachoa* sp.
- *Designation*.—'KLECA20810'.

Parentage:
- *Female parent*.—'KLECA17029' (U.S. Plant Pat. No. 30,836).
- *Male parent*.—'CA-2016-8001' (unpatented).

Plant:
- *Life cycle*.—Annual.
- *Form*.—Short-lived subshrub.
- *Habit*.—Semi-trailing.
- *Height* (*from soil line to top of foliage*).—17.5 cm.
- *Spread*.—46.0 cm.
- *Propagation type*.—Vegetative tip cuttings.
- *Time to produce a rooted cutting*.—3 weeks.
- *Pests and disease resistance*.—No particular pest or disease resistance observed to date.

Stems:
- *Stem color*.—RHS 143C (Yellow-Green).
- *Pubescence*.—Present.
- *Pubescence color*.—RHS 155A (White).
- *Stem diameter*.—0.1 cm.

*Stem length*.—From soil line to first node: 1.5 cm. Total length: 35.0 cm.
*Internode length*.—2.1 cm.

Foliage:
*Arrangement*.—Opposite.
*Shape*.—Lanceolate.
*Apex*.—Obtuse.
*Base*.—Obtuse.
*Margin*.—Ciliate.
*Variegation*.—Absent.
*Surface texture*.—Upper surface: Smooth. Lower surface: Pubescence is moderate.
*Pubescence color*.—RHS 155A (White).
*Venation*.—Pinnate.
*Venation color*.—Upper surface: RHS 137A (Green). Lower surface: RHS 138B (Green).
*Length*.—2.7 cm.
*Width*.—0.3 cm to 0.8 cm.
*Color*.—Upper surface: RHS 137A (Green). Lower surface: RHS 138B (Green).
*Fragrance*.—Absent.
*Petiole*.—Absent; sessile.

Inflorescence:
*Flowering type*.—Single flowers.
*Flowering requirements*.—A minimum of light sun is required.
*Flowering season*.—Continuous flowering from spring through autumn and all the time or year around in a greenhouse environment.
*Duration of flowers*.—6 days.
*Corolla texture*.—Smooth.
*Shape*.—Funnel form.
*Lobing of the flower*.—Weak.
*Fragrance*.—Absent.
*Flowers per plant*.—About 36 to 40.
*Flower depth*.—2.5 cm.
*Flower diameter*.—3.5 cm.
*Flower tube length*.—1.1 cm.
*Flower tube diameter*.—0.4 cm.
*Flower throat diameter*.—0.7 cm.
*Pedicel color*.—RHS 143C.
*Pedicel length*.—2.2 cm.

Flower bud:
*Surface texture*.—Smooth.
*Typical number of buds per plant at any time*.—About 35.
*Length*.—2.1 cm.
*Diameter*.—0.4 cm.
*Shape*.—Irregular to oblong.
*Color*.—RHS N155C (White).

Peduncles:
*Length*.—1.8 cm to 3.0 cm.
*Diameter*.—0.1 cm.
*Color*.—RHS 143C (Yellow-Green).
*Texture*.—Pubescent.
*Anthocyanin color*.—Absent.

Sepals:
*Calyx*.—Funnel-shaped, salver-form.
*Shape*.—Lanceolate.
*Surface texture* (*both upper and lower surfaces*).—Pubescent.
*Quantity per flower*.—5.
*Apex*.—Obtuse.
*Base*.—Fused.
*Margin*.—Ciliate.
*Length*.—1.35 cm.
*Diameter*.—0.25 cm.
*Sepal color*.—Upper surface: RHS 138A (Green). Lower surface: RHS 138A (Green).

Petals:
*Shape*.—Obcordate.
*Quantity per flower*.—5 fused petals, each petal comprised of 2 lobes.
*Length* (*without tube*).—1.2 cm.
*Apex*.—Truncate.
*Margin*.—Entire.
*Base*.—Fused into the tube.
*Texture*.—Upper surface: Smooth. Lower surface: Smooth.
*Lobe length*.—1.5 cm.
*Lobe width*.—1.5 cm.
*Color*.—Lobe color: Upper surface: RHS 68A (Red-Purple) and fading to RHS N74D (Red-Purple); transition color is RHS N66A (Red-Purple), with RHS 77A (Purple) centers and RHS 9A (Yellow) stripes; transition area is medium in size and rounded. Lower surface: RHS 73D (Red-Purple) fading to RHS 76D (Purple); transition area is RHS 72B (Red-Purple) and fades to RHS 73D (Red-Purple); transition area is medium in size and rounded; vein color is RHS 173A (Greyed-Orange) and fades to RHS 199A (Grey-Brown). Corolla tube color: Inner surface: RHS 5A (Yellow) with RHS 77A (Purple) veins. Outer: RHS 4B (Yellow) with RHS 173A (Greyed-Orange) veins.
*Fragrance*.—Absent.

Reproductive organs:
*Stamen number*.—5.
*Anther color*.—RHS 11B (Yellow).
*Anther shape*.—Bi-lobed and ovoid.
*Anther length*.—Less than 0.1 cm.
*Filament color*.—RHS 149D (Yellow-Green).
*Filament length*.—0.8 cm.
*Pollen color*.—RHS 11B (Yellow).
*Pollen amount*.—Moderate.
*Placenta arrangement*.—Basal.
*Pistil number*.—1.
*Pistil length*.—0.9 cm.
*Stigma color*.—RHS 143B (Green).
*Stigma shape*.—Rounded.
*Style length*.—0.8 cm.
*Style color*.—RHS 145C (Yellow-Green).

Fruit and seed set: No fruit or seed set observed.

COMPARISON OF 'KLECA20810' WITH PARENTAL LINES AND KNOWN VARIETY

'KLECA20810' is a distinct variety of *Calibrachoa* and is distinguished from its parents as described in Table 1.

TABLE 1

Comparison with Parental Lines

| Characteristic | 'KLECA20810' | Female Parent 'KLECA17029' | Male Parent 'CA-2016-8001' |
|---|---|---|---|
| Flower size | Larger than the female parent | Medium | Medium |
| Habit | More compact than the female parent | Less compact than 'KLECA20810' | Less compact than 'KLECA20810' |

TABLE 1-continued

| Comparison with Parental Lines | | | |
|---|---|---|---|
| Characteristic | 'KLECA20810' | Female Parent 'KLECA17029' | Male Parent 'CA-2016-8001' |
| Vigor | Medium Vigorous than the female parent | Vigorous | Medium vigor |

'KLECA20810' is a distinct variety of *Calibrachoa* and differences between 'KLECA16006' (U.S. Plant Pat. No. 29,433) also known as RAVE 'Pink 16' are described in Table 2.

TABLE 2

| Comparison with Similar Variety | | |
|---|---|---|
| Characteristic | 'KLECA20810' | 'KLECA16006' |
| Earliness to flower | Flowers 3 days earlier than 'KLECA16006' | Flowers 3 days later than 'KLECA20810' |
| Flower size | Larger than 'KLECA16006' | Smaller than 'KLECA20810' |
| Habit | More compact than 'KLECA16006' | Less compact than 'KLECA20810' |

I claim:

1. A new and distinct variety of *Calibrachoa* plant designated 'KLECA20810' as illustrated and described herein.

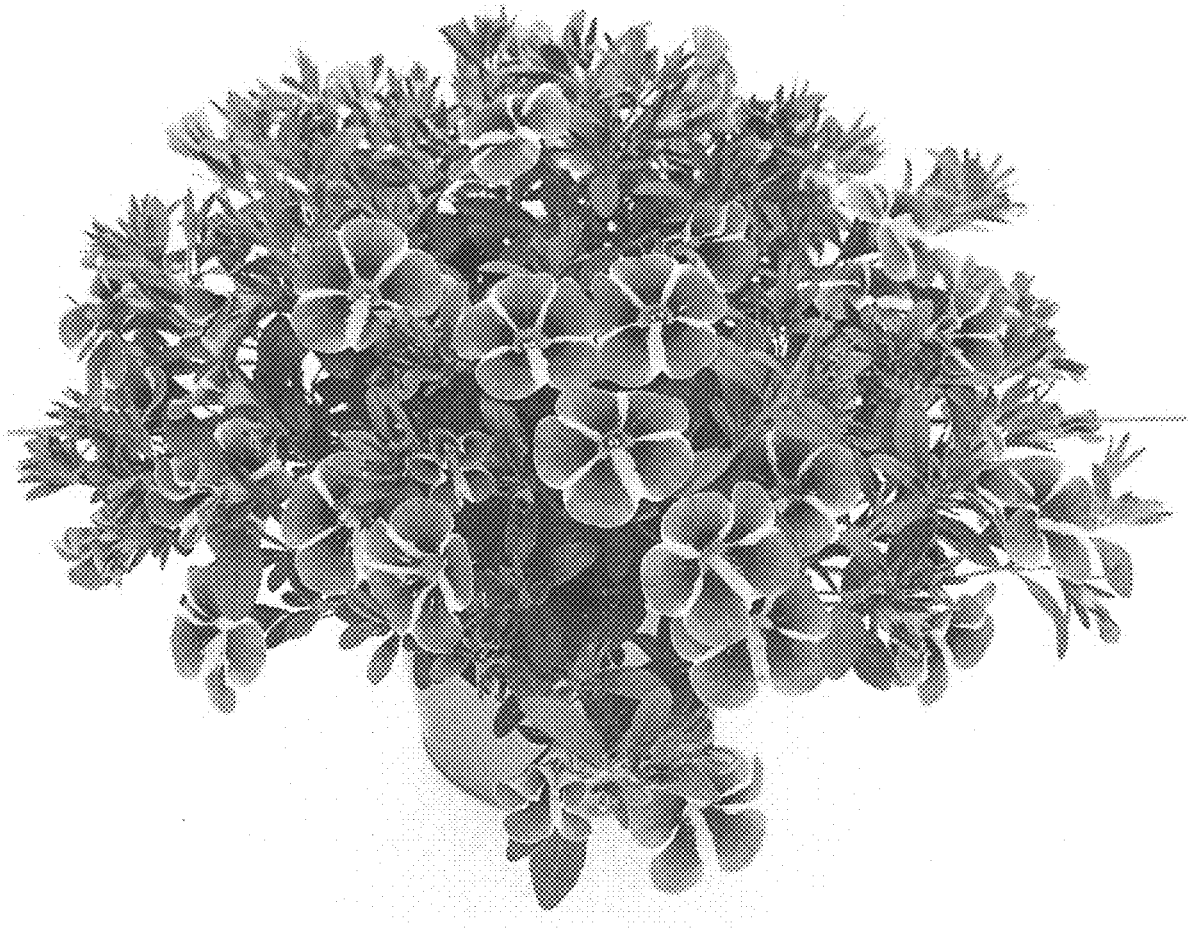

* * * * *